United States Patent
Hoving et al.

(12) 
(10) Patent No.: US 6,576,275 B1
(45) Date of Patent: Jun. 10, 2003

(54) PROCESS FOR EXTRACTING POLYPHENOLIC ANTIOXIDANTS FROM PURINE-CONTAINING PLANTS

(75) Inventors: Hendrik Derk Hoving, Maastricht (NL); Hans Robert Kattenberg, Krommenie (NL); Dick Antonius Johannes Starmans, Wageningen (NL)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 09/890,664

(22) PCT Filed: Feb. 2, 2000

(86) PCT No.: PCT/US00/02411

§ 371 (c)(1), (2), (4) Date: Jan. 16, 2002

(87) PCT Pub. No.: WO00/45769

PCT Pub. Date: Aug. 10, 2000

(30) Foreign Application Priority Data

Feb. 2, 1999 (EP) .............................................. 99200301

(51) Int. Cl.$^7$ ................................................ A61K 35/78
(52) U.S. Cl. ...................... 424/776; 424/725; 424/729
(58) Field of Search .............................. 424/725, 729, 424/776

(56) References Cited

U.S. PATENT DOCUMENTS

| | | | |
|---|---|---|---|
| 4,390,698 A | 6/1983 | Chiovini et al. ............. | 544/274 |
| 4,444,798 A | 4/1984 | Magnolato et al. ......... | 426/422 |
| 4,481,223 A | * 11/1984 | Hinman et al. | |
| 4,704,292 A | 11/1987 | Kattenberg ................. | 426/565 |
| 4,755,391 A | 7/1988 | Bigalli et al. ................ | 426/427 |
| 4,956,429 A | 9/1990 | Harmetz et al. ............ | 426/271 |
| 5,021,253 A | * 6/1991 | Dawson-Ekeland et al. | |
| 5,141,611 A | 8/1992 | Ford ........................ | 204/182.4 |
| 5,328,708 A | 7/1994 | Rizzi et al. ................ | 426/388 |
| 5,554,645 A | 9/1996 | Romanczyk, Jr. et al. .. | 514/453 |
| 5,712,305 A | 1/1998 | Romanczyk, Jr. et al. .. | 514/453 |
| 5,877,206 A | 3/1999 | Romanczyk, Jr. et al. .. | 514/453 |
| 5,888,562 A | * 3/1999 | Hansen et al. | |
| 5,891,905 A | 4/1999 | Romanczyk, Jr. et al. .. | 514/449 |
| 6,001,406 A | * 12/1999 | Katzke et al. | |
| 6,015,913 A | 1/2000 | Kealey et al. ............... | 549/386 |
| 6,156,791 A | 12/2000 | Romanczyk, Jr. et al. .. | 514/453 |
| 6,194,020 B1 | 2/2001 | Myers et al. ............... | 426/631 |
| 6,210,679 B1 | * 4/2001 | Bailey et al. | |
| 6,225,338 B1 | 5/2001 | Romanczyk, Jr. et al. .. | 514/453 |

FOREIGN PATENT DOCUMENTS

| | | | |
|---|---|---|---|
| BR | 9 303 217 A | | 3/1995 |
| JP | 62061569 | * | 3/1987 |
| JP | 5-260907 | | 10/1993 |
| JP | 9-220053 | | 8/1997 |
| WO | WO 96/10404 | | 4/1996 |
| WO | WO 96/28178 | * | 9/1996 |
| WO | WO 98/09533 | | 3/1998 |
| WO | WO 98/42209 | | 10/1998 |

OTHER PUBLICATIONS

English language translation of Japanese Patent Application No. 5–260907, filed Mar. 17, 1992 and published Oct. 12, 1993.

English language abstract of JP 5–260907 (Document AL1), Application No. JPO4090107, filed Mar. 17, 1992 and published Oct. 12, 1993, JPO and Japio.

English Language Abstract of JP 06 009607 A, Application No. 05096518, filed Apr. 1, 1993 and published Jan. 18, 1994, JPO.

English Language Abstract of JP 10 067771 A, Application No. 08241012, filed Aug. 26, 1996 and published Mar. 10, 1998, JPO.

English Language Abstract of JP 09 110712 A, Application No. 07272404, filed Oct. 20, 1995 and published Apr. 28, 1997, JPO.

English Language Abstract of JP 09 220053 A, Application No. 08028235, filed Feb. 15, 1996 and published Aug. 26, 1997, JPO.

English Language Abstract of BR 9303217–0A, Application No. BR 933217, filed Jul. 30, 1993 and published Mar. 1, 1995, Derwent Publications Ltd.

Kashiwada, Y. et al., "Tannins as Potent Inhibitors of DNA Topoisomerase II in Vitro," *Journal of Pharmaceutical Sciences* 82:487–492, American Pharmaceutical Association (1993).

Naito, S. et al., "Fractionation of Antioxidants from Cacao Bean Husk (Studies on Natural Antioxidant Part IV)," *Nippon Shokuhin Kogyo Gakkaishi* 29:529–533, Japanese Society of Food Science and Technology (1982).

De Oliveira, M.M. et al., "Antitumor Activity of Condensed Flavanols," *An. Acad. Brasil Ciênc.* 44:41–44, Academia Brasileira de Ciências (1972).

Porter, L.J. et al., "Cacao Procyanidins: Major Flavanoids and Identification of Some Minor Metabolites," *Phytochemistry* 30:1657–1663, Pergamon Press (1991).

Wang, Z.Y. et al., "Inhibitory Effect of Green Tea on the Growth of Established Skin Papillomas in Mice," *Cancer Research* 52:6657–6665, American Association for Cancer Research (1992).

* cited by examiner

Primary Examiner—Christopher R. Tate
(74) Attorney, Agent, or Firm—Sterne, Kessler, Goldstein & Fox P.L.L.C.

(57) ABSTRACT

A process for isolating polyphenolic antioxidants from purine-containing plant material, comprising the steps of: (a) extracting the plant material with a hydroxylic extracting liquid preferably at low temperature; (b) selectively adsorbing the extract obtained in step (a), preferably at low temperature; and (c) desorbing the adsorbed material with a hydroxylic desorbing liquid, preferably at relatively high temperature. The process is especially suitable for producing cocoa antioxidants of use in pharmaceutical, cosmetic and nutritional compositions.

17 Claims, 1 Drawing Sheet

PROCESS FOR EXTRACTING POLYPHENOLIC ANTIOXIDANTS FROM PURINE-CONTAINING PLANTS

CROSS REFERENCE TO RELATED APPLICATIONS

The present application is the National Phase of International Application No. PCT/US00/02411, filed Feb. 2, 2000, which was published in English.

BACKGROUND OF THE INVENTION

1. Field of the Invention

The present invention relates to a process for producing polyphenolic antioxidants with low purine content, from cocoa and other purine-containing plant materials. The invention also relates to an antioxidant composition obtainable using this process. The invention further relates to a nutritional, pharmaceutical or cosmetic antioxidant composition.

2. Related Art

Polyphenolic antioxidants from plant materials derived from cocoa, coffee, tea, and other theobroma species are interesting as they are assumed to be active in preventing cancer, coronary and cardiovascular disease and strokes, and in delaying aging processes. These antioxidants are usually water-soluble and comprise compounds of the chroman type, such as catechin and epicatechin (the stereoisomeric 2-(3,4-dihydroxyphenyl)-3,5,7-trihydroxychromans), and oligomerised structures including procyanidin. However, these plant materials also contain purines such as caffeine (1,3,7-trimethyl-2,6-purinedione or 1,3,7-trimethylxanthine) and theobromine (3,7-dimethyl-2,6-purinedione or 3,7-dimethylxanthine), and these components are usually undesired in antioxidant compositions because of their stimulating properties.

Current processes for extracting polyphenols from cocoa comprise treatment of defatted cocoa material with acetone, water/methanol, chloroform and ethyl acetate. Such a process is described in WO 98/09533 (Mars Inc.). A process for removing purines (theobromine and caffeine) from cocoa material by extraction with water of 45–55° C. followed by extraction with water of about 100° C. is described in U.S. Pat. No. 4,755,391 (Hershey Foods Corp.).

Japanese patent application JP-A-6-9607 concerns the production of tea catechins. The method consists of extracting tea leaves with water, non-selectively adsorbing the purines and catechins on a gel-type adsorbent (e.g., styrene/divinylbenzene) in a column, washing the purines (caffeine) from the column using warm water, and desorbing the catechins from the column using 50–100% aqueous methanol, ethanol or acetone.

Japanese patent application JP-A-10-67771 similarly concerns the production of tea catechins, by non-selectively adsorbing the constituents of a tea extract on a column containing cyclodextrin bound to a crosslinked acrylic resin, and again washing the purines with water and desorbing the catechins with 30–80% aqueous methanol, ethanol or acetone.

Methylxanthines (purines) are usually extracted with chlorinated hydrocarbon solvents, such as chloroform, ethylene dichloride or tetrachloroethane. Methylxanthines are also removed by adsorption on an adsorption material like activated carbon, carob particles or a cation exchange resin as described in U.S. Pat. Nos. 4,956,429, 4,390,698 and 4,444,798.

The problem to be solved with the present invention was to provide a process for producing a natural, fat-free, water-soluble polyphenolic antioxidant composition having a maximum antioxidant activity and a minimum purine content, said process being technically and economically feasible without the use of objectionable chemicals.

SUMMARY OF THE INVENTION

The present invention relates to a process for producing polyphenolic antioxidants with low purine content, from cocoa and other purine-containing plant materials, as well as an antioxidant composition obtainable using this process. The invention further relates to a nutritional, pharmaceutical or cosmetic antioxidant composition.

The present invention provides a process for producing a natural, fat-free, water-soluble polyphenolic antioxidant composition having a maximum antioxidant activity and a minimum purine content. This process is technically and economically feasible without the use of objectionable chemicals.

DETAILED DESCRIPTION

Figure 1:
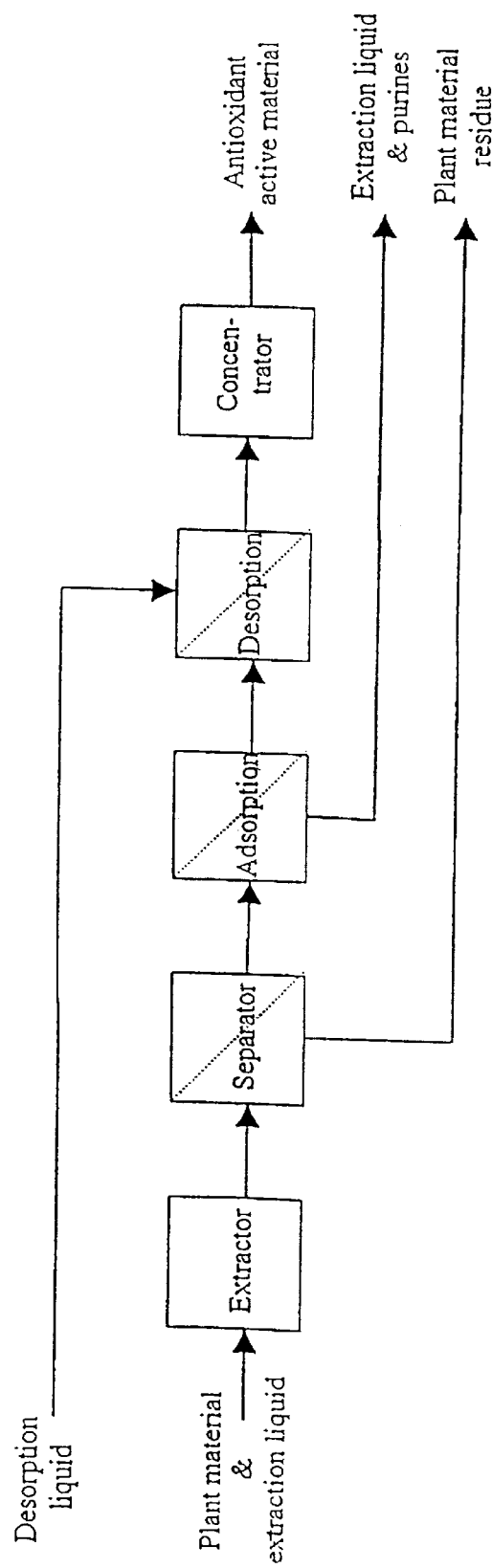
FIG. 1 shows the process of the invention illustrated by a flow diagram.

The process of the invention is characterized by the features of the appending claims, and comprises the steps of:

(a) extracting the plant material with a hydroxylic extracting liquid, preferably at a temperature below 50° C.;

(b) selectively adsorbing the extract obtained in step (a), preferably at a temperature below 30° C.; and (c) desorbing the adsorbed material with a hydroxylic desorbing liquid, preferably at a temperature above 30° C.

The process of the invention can be used for extracting polyphenolic antioxidants from purine-containing materials, in particular, tea and tea derivatives, (e.g., *Camellia sinensis, C. assamica*), coffee beans (*Coffea arabica, C. aniphora, C. robusta, C. liberica*) and derivatives thereof and cocoa beans (*Theobroma cacao*) and cocoa derivatives. The latter include beans from other Theobroma species like *T. grandiflora*. Coffee and especially cocoa products are the preferred starting materials. The starting cocoa products may be, e.g., fresh beans, defatted solids, comminuted trash beans, cocoa powder, low-fat cocoa powder, cocoa shells, cocoa waste or other raw materials. The starting material is preferably ground to a particle size below 250 $\mu$m.

An essential feature of the present invention is the use of an adsorption material that has a high polyphenol/purine adsorption selectivity. This relative selectivity, expressed as polyphenolic antioxidant/purine adsorption ratio for a hydroxylic plant extract, is in particular at least 5/1, especially at least 9/1. Under selected conditions, the adsorbent thus has a minimum adsorption of the methylxanthines and a maximum adsorption of the polyphenolic antioxidants from the extract. The polyphenolic antioxidants thus selectively adsorbed are subsequently desorbed and concentrated. The present invention results in the production of a high grade antioxidant composition having a low purine content without the use of questionable chemicals and solvents; residues of these are most undesirable in medicinal, nutraceutical, nutritional and pharmaceutical applications. The process of the invention permits yields of the valuable polyphenolic compounds exceeding 70%, or even of 80% and higher.

The adsorbent to be used for selectively adsorbing polyphenolic compounds is preferably polyvinylpolypyrrolidone (PVPP), i.e., crosslinked polyvinylpyrrolidone, or a derivative or modification thereof. Examples of chemical modifications of PVPP are the common nucleophilic substitution reactions on the carbonyl group like reactions with alcohols (acetal formation), amines (Schiff base formation) and phosphorous ylids (Wittig reaction), and the reduction of the carbonyl group using $LiAlH_4$. The purpose of the modification is to modify the adsorption characteristics of PVPP by changing the hydrophobicity of the PVPP material. Examples of physical modification of PVPP are controlled expansion using liquified or supercritical gases, grinding or solvent treatment of the PVPP matrix. The purpose of such treatments is to increase the surface area per gram of material and/or to modify gravimetric separation properties when using the PVPP in a combined extraction/adsorption step. PVPP of the commercially available grade is suitable. Other suitable adsorbents include chitosan and blends between PVPP and chitosan or chemical or physical derivatives thereof. The amount of adsorbent to be used can be, e.g., between 0.2 and 200 g, preferably between 5 and 50 g per liter of extract.

Prior to the adsorption step, the polyphenolic antioxidants are extracted from the plant material using a hydroxylic solvent, preferably water. The temperature of the extraction can be varied. A significant characteristic of the process of the invention is that if the plant material is extracted at low temperatures, a minimal extraction of purines and maximal extraction of the antioxidants is obtained. Thus the selectivity of the process of the invention can be further increased by using low extraction temperatures, i.e., below 50° C., especially below 30° C., and preferably between 0 and 30° C. However, a higher extraction temperature (e.g., around 70° C.) may be used in order to control microbial contamination.

The hydroxylic solvent to be used according to the invention is a solvent which selectively extracts polyphenolic compounds. It is selected from water and lower alcohols, such as methanol, ethanol, propanol, isopropanol, one of the isomeric butanols, methoxyethanol, glycol and the like. The preferred extracting liquid is water or ethanol or a mixture thereof; most preferred is water. The preferred desorbing liquid is water or a water-miscible alcohol or a mixture thereof, or a mixture of water and a water-miscible ketone. Most preferred desorbing liquids are mixtures of water and a lower alcohol, diol or ketone, such as water/methanol, water/ethanol, water/isopropanol, water/methoxyethanol, water/glycol, water/acetone, water/methylethylketone, water/ethanol/glycol, etc., with volume ratios between 10/90 and 90/10, especially between 15/85 and 80/20, the first number being the water percentage. Other hydroxylic substances such as glycerol, sorbitol, glucose, sucrose, lactose, maltose, maltodextrins etc., may be added to further enhance desorption. Such hydroxylic substances may also serve as a carrier in the subsequent drying process, or in the final product, if desired. The amount of extracting liquid can be e.g., between 5 and 50 times (w/w) the amount of starting plant material. The desorption can be carried out at a pH between 4 and 9, especially at about neutral pH (5.5–8). The desorption step is carried out at a temperature above 30° C., preferably at a temperature between 50° C. and 110° C.

The desorbed material can subsequently be concentrated. The main part of the desorption liquid can be evaporated (under partial vacuum if necessary). The antioxidant active material can then be dried using freeze-drying and/or vacuum distillation.

The antioxidant activity of the product can be expressed in the capability to scavenge free radicals. This capacity can be expressed towards Trolox, 6-hydroxy-2,5,7,8-tetramethylchromane-2-carboxylic acid, a water-soluble variant of vitamin E, in TEAC (Trolox Equivalent Antioxidant Capacity) as is also presented by Salah et al., *Arch. Biochem. Biophys.* 322(2):339–346 (1995).

The antioxidant composition that can be obtained with the process of the invention has at least a TEAC value of 0.4 and less than 5% by weight of purine components. In particular, the composition obtainable by the process of the invention has at least a TEAC value of 0.6 and less than 3.5% by weight of purine components. Especially the level of caffeine is less than 1.0%, in particular less than 0.5% for cocoa-derived products. The product contains at least 15%, preferably at least 20%, especially at least 25% by weight of polyphenolic antioxidants. For cocoa-derived products, these comprise essentially catechin and epicatechin. For coffee-derived products, these may further comprise chlorogenic acid and its isomers, in addition to epicatechin. The TEAC value of the product may be at least 0.8 and as high as about 1.5. The product is free of (i.e., contains less than 10 ppm (w/w), in particular less than 1 ppm, or even less than 0.5 ppm of) chlorinated hydrocarbons and is substantially fat-free (i.e., contains less than 0.5 wt. % of fat).

The antioxidant product can be used as an ingredient for nutritional products and can be used as a basic substance for, e.g., chocolate bars, beverages, confectionary, ice-cream and pastries. The product can also be used in medicinal, nutraceutical, pharmaceutical and cosmetic (e.g., skin care) formulations.

The process of the invention is further illustrated by the flow diagram in the accompanying FIG. 1. The process for the production of antioxidants consists of a (consecutive or counter-current) extraction of plant material with a hydroxylic solvent followed by separation of the extract. Separation may be achieved by filtration, ultrafiltration or centrifugation, depending on the desired clarification and purity. After separation, the extract should be clear and free of solid or colloidal particles. The extract is then subjected to a selective adsorption section where the polyphenolic antioxidants are adsorbed on adsorption material. The hydroxylic solvent with the unadsorbed purines can be recycled. Another possibility is the combination of extraction and adsorption with the addition of the material to the extract/solids mixture and subsequent physical separation of the adsorption material from this mixture. Desorption also takes places with a hydroxylic and/or ketonic solvent. Desorption can be done by placing the adsorption material in a column and then performing (consecutive) washings or bed spraying. Another desorption technique is immersing extraction of the adsorption material. The desorbed solution of active components may be further concentrated and/or dried as desired by any technical means available, like evaporation whether or not under reduced pressure, vacuum distillation, reversed osmosis, freeze-drying or spray-drying.

EXAMPLE 1

Immersion Extraction of Cocoa Powder at Different Temperatures

In a 1000 ml conical flask, 50 grams of cocoa powder, of the N-11-N type, containing 10.5% fat was mixed with 500 gram of demineralised water. The set point temperature was maintained with a temperature controller. Homogeneous samples of 10 ml were taken after 15 minutes. The extraction was conducted at 20, 40, 60, 80, and 100° C. The concentrations of theobromine (THB), caffeine (CAF), catechin (CAC), and epicatechin (EPC) in the samples were analysed with a HPLC, using a Waters symmetric 4.6×250 mm C18 15 µm column, a photodiode array detector at 276 nm, a flow rate of 1.5 ml/min and a column temperature of 35° C. The mobile phase was a varying gradient 2.5 vol. % acetic acid and 30 vol. % acetonitrile in water.

TABLE 1

Influence of temperature on the extraction of cocoa (in g/l)

| Temperature (° C.) | THB | CAF | CAC | EPC |
|---|---|---|---|---|
| 20 | 1.21 | 0.06 | 0.15 | 0.1 |
| 40 | 1.73 | 0.06 | 0.14 | 0.09 |
| 60 | 2.17 | 0.07 | 0.15 | 0.1 |
| 80 | 2.39 | 0.07 | 0.14 | 0.08 |
| 100 | 2.43 | 0.07 | 0.15 | 0.08 |

Table 1 shows the surprising tendency that the extraction performance of the antioxidants does not significantly vary within the temperature range of 20–100° C. The undesired purines, mainly theobromine, display the lowest extraction performance at 20° C. Therefore, an extraction temperature below 30° C. will result in a minimum extraction of purines and a maximum extraction of antioxidants, for the described type of cocoa powder.

EXAMPLE 2

Adsorption of a Cocoa Extract on PVPP Followed by Desorption and Freeze-drying

Natural cocoa powder, which is rich in catechins, was extracted with demineralised water at 20° C. for three hours at a ratio of 10 w/w. An amount of 400 gram extract was mixed (magnetic stirrer) with 4 gram crosslinked PVPP (CAS 25249-54-1 obtained from Akcros) at 5° C. during 90 min. The adsorbed material was then separated using a glass filter (por. 0). This was placed in a Soxhlet apparatus and refluxed with demineralised water for 24 hours. Subsequently, the extract was subjected to freeze-drying, resulting in a dry cocoa material enriched in antioxidant activity. The concentrations of theobromine (THB), caffeine (CAF), catechin (CAC), and epicatechin (EPC) in the samples were analysed by HPLC. The antioxidant activity was measured using the DPPH radical scavenging method (Brand-Williams et al., *Lebensmittel-Wissenschaft und Technologie* 28:25–30 (1995)). This method measures the adsorbance before and after (4 hours) the addition of an antioxidant to an ethanolic solution of DPPH radicals. This radical has a deep purple colour and absorbs at 515 mn. Trolox was used as a reference antioxidant and the TEAC values are based on the amount (in g) of antioxidant-active material that equals the amount (in g) of Trolox necessary for scavenging 50% of the DPPH radicals. Trolox and DPPH were obtained from Fluka Chemika.

TABLE 2

Performance of the adsorption

| | THB | CAF | CAC | EPC |
|---|---|---|---|---|
| Adsorption efficiency [%] | 1 | 10 | 100 | 96 |

Table 2 shows the adsorption efficiency of the adsorption of the four relevant cocoa components theobromine, caffeine, catechin and epicatechin from the cocoa extract with PVPP. Bringing the aqueous cocoa extract in contact with the PVPP adsorbent results in a surprisingly low interaction of the purines with the adsorbent and in a selective adsorption of catechin and epicatechin. Table 3 shows the composition of the initial cocoa material, and the final product composition in the final product after freeze-drying, including TEAC values. The "other" material also comprises polyphenolic antioxidants (presumably about 20 wt. %).

TABLE 3

Overall performance of antioxidant production

| | THB [wt. %] | CAF [wt. %] | CAC [wt. %] | EPC [wt. %] | other [wt. %] | TEAC [g] |
|---|---|---|---|---|---|---|
| Starting composition [wt. %] | 3 | 0.3 | 0.3 | 1.2 | 95 | 0.05 |
| Product composition [wt. %] | 3 | 0.4 | 19 | 11 | 67 | 1 |

What is claimed is:

1. A process for isolating polyphenolic antioxidants from purine containing plant material, comprising:

(a) extracting the plant material with a hydroxylic extracting liquid at a temperature below 50° C., wherein the hydroxylic extracting liquid comprises water and/or a lower alcohol;

(b) selectively adsorbing the extract obtained in step (a) on a solid adsorbent which has a polyphenol to purine adsorption selectivity ratio of at least 5 to 1, respectively;

(c) desorbing adsorbed material obtained in step (b) with a hydroxylic desorbing liquid at a temperature between 50 and 110° C., thereby isolating the polyphenolic antioxidants.

2. A process according to claim 1, in which the desorbed material is concentrated and optionally dried.

3. A process according to claim 1, in which the adsorbent comprises polyvinylpolypyrrolidone or a chemical or physical modification thereof.

4. A process according to claim 1, in which the adsorbent comprises chitosan or a chemical or physical modification thereof.

5. A process according to claim 1, in which step (a) is carried out at a temperature between 0 and 30° C.

6. A process according to claim 1, in which step (b) is carried out at a temperature below 30° C.

7. A process according to claim 1, in which the hydroxylic desorbing liquid in step (c) comprises water and a lower alcohol or water and a lower ketone.

8. A process according to claim 1, in which said purine-containing plant material is cocoa, coffee, or tea.

9. A process for isolating polyphenolic antioxidants from cocoa, comprising:

(a) extracting the plant material with a hydroxylic extracting liquid at a temperature below 50° C., wherein the hydroxylic extracting liquid comprises water and/or a lower alcohol;

(b) selectively adsorbing the extract obtained in step (a) on a solid adsorbent which has a polyphenol to purine adsorption selectivity ratio of at least 5 to 1, respectively;

(c) desorbing adsorbed material obtained in step (b) with a hydroxylic desorbing liquid, thereby isolating the polyphenolic antioxidants.

10. A process according to claim 9, in which the desorbed material is concentrated and optionally dried.

11. A process according to claim 9, in which the adsorbent comprises polyvinylpolypyrrolidone or a chemical or physical modification thereof.

12. A process according to claim 9, in which the adsorbent comprises chitosan or a chemical or physical modification thereof.

13. A process according to claim 9, in which step (a) is carried out at a temperature between 0 and 30° C.

14. A process according to claim 9, in which step (b) is carried out at a temperature below 30° C.

15. A process according to claim 9, in which step (c) is carried out at a temperature above 30° C.

16. A process according to claim 9, in which step (c) is carried out at a temperature between 50 and 110° C.

17. A process according to claim 9, in which the hydroxylic desorbing liquid in step (c) comprises water and a lower alcohol or water and a lower ketone.

* * * * *